(12) United States Patent
Hu et al.

(10) Patent No.: US 11,998,764 B2
(45) Date of Patent: Jun. 4, 2024

(54) EXTRACORPOREAL FOCUSED ULTRASOUND TREATMENT DEVICE FOR PELVIC DISEASE

(71) Applicant: CHONGQING HAIFU MEDICAL TECHNOLOGY CO., LTD., Chongqing (CN)

(72) Inventors: Hongbing Hu, Chongqing (CN); Fangwei Ye, Chongqing (CN); Bing Fu, Chongqing (CN); Zhengming Cheng, Chongqing (CN); Ying Zou, Chongqing (CN); Hongjun Wen, Chongqing (CN); Xiaobing Wu, Chongqing (CN); Liang Hu, Chongqing (CN); Haoran Huang, Chongqing (CN); Jun Sun, Chongqing (CN); Zheng Hu, Chongqing (CN); Wenying Ma, Chongqing (CN)

(73) Assignee: CHONGQING HAIFU MEDICAL TECHNOLOGY CO., LTD., Chongqing (CN)

( * ) Notice: Subject to any disclaimer, the term of this patent is extended or adjusted under 35 U.S.C. 154(b) by 966 days.

(21) Appl. No.: 16/963,280

(22) PCT Filed: Sep. 7, 2018

(86) PCT No.: PCT/CN2018/104623
§ 371 (c)(1),
(2) Date: Jul. 20, 2020

(87) PCT Pub. No.: WO2019/140928
PCT Pub. Date: Jul. 25, 2019

(65) Prior Publication Data
US 2021/0361976 A1    Nov. 25, 2021

(30) Foreign Application Priority Data

Jan. 22, 2018  (CN) .......................... 201810059205.5

(51) Int. Cl.
*A61N 7/00* (2006.01)
*A61G 13/00* (2006.01)

(52) U.S. Cl.
CPC ............. *A61N 7/00* (2013.01); *A61G 13/009* (2013.01); *A61N 2007/0004* (2013.01); *A61N 2007/0052* (2013.01); *A61N 2007/0069* (2013.01)

(58) Field of Classification Search
CPC ........................ A61G 15/005; A61B 2090/378
See application file for complete search history.

(56) References Cited

U.S. PATENT DOCUMENTS

| 8,649,242 B2 | 2/2014 | Martin et al. |
| 9,242,121 B2 | 1/2016 | Wang et al. |

(Continued)

FOREIGN PATENT DOCUMENTS

| CN | 2503917 Y | 8/2002 |
| CN | 2889239 Y | 4/2007 |

(Continued)

OTHER PUBLICATIONS

KR-1801900-B1 (Year: 2017).*
CN-103520844-A (Year: 2014).*

*Primary Examiner* — Joel Lamprecht
*Assistant Examiner* — Nyrobi Celestine
(74) *Attorney, Agent, or Firm* — The Webb Law Firm

(57) ABSTRACT

The present disclosure provides an extracorporeal focused ultrasound treatment device for a pelvic disease. The treatment device includes an ultrasonic transducer and a treatment couch. Sound emitting surface of the ultrasonic transducer is a spherical surface having a first notch, a second notch and a third notch, the first notch and the second notch are respectively positioned at two intersections of the spherical surface and a diameter perpendicular to the main great circle, and the third notch connects the first notch with the (Continued)

second notch; a cross-section of the sound emitting surface parallel to the main great circle is in a shape of an arc; and an ultrasonic wave generated by the sound generation unit is focused at a center of the sphere corresponding to the sound emitting surface. The treatment couch is configured for a human body to lie in a lithotomy position.

18 Claims, 8 Drawing Sheets

(56) References Cited

U.S. PATENT DOCUMENTS

| | | | |
|---|---|---|---|
| 2005/0107702 A1* | 5/2005 | He | A61N 7/02 601/3 |
| 2006/0058678 A1 | 3/2006 | Vitek et al. | |
| 2017/0119481 A1* | 5/2017 | Romo | A61B 17/320758 |
| 2018/0085271 A1* | 3/2018 | Lim | A61G 15/02 |

FOREIGN PATENT DOCUMENTS

| | | | | |
|---|---|---|---|---|
| CN | 101855572 A | | 10/2010 | |
| CN | 102210910 A | | 10/2011 | |
| CN | 103520844 A | * | 1/2014 | |
| CN | 103520844 A | | 1/2014 | |
| KR | 1801900 B1 | * | 11/2017 | A61B 8/463 |

* cited by examiner depth of 80mm-400W-2s

EXTRACORPOREAL FOCUSED ULTRASOUND TREATMENT DEVICE FOR PELVIC DISEASE

CROSS-REFERENCE TO RELATED APPLICATIONS

This application is the United States national phase of International Application No. PCT/CN2018/104623 filed Sep. 7, 2018, and claims priority to Chinese Patent Application No. 201810059205.5 filed Jan. 22, 2018, the disclosures of which are hereby incorporated by reference in their entirety.

BACKGROUND OF THE INVENTION

Field of the Invention

The present disclosure belongs to the field of high intensity focused ultrasound treatment technology, and particularly relates to an extracorporeal focused ultrasound treatment device for a pelvic disease.

Description of Related Art

High Intensity Focused Ultrasound (HIFU) technology has been widely used to treat benign and malignant tumors such as liver cancer, breast cancer, kidney cancer, bone tumor, uterine fibroid, etc. By using the focusability and penetrability of ultrasound, ultrasound is focused at a lesion site in a human body, and high energy density mechanical energy in the focal region is converted into heat energy to cause coagulative necrosis (also called ultrasound thermal ablation) of diseased tissues; meanwhile, because the ultrasonic energy density on the beam path is low, it can be guaranteed that influence on normal tissues around the diseased tissues and on the beam path is little or acceptable.

Most of existing focused ultrasonic transducers for extracorporeal high intensity focused ultrasound treatment have a sound emitting surface in the shape of a spherical cap, and ultrasound emitted from the existing focused ultrasonic transducer is a traveling wave. The focal region formed by the existing ultrasound transducer has a shape similar to a cigar or a spindle, its length in the direction of the sound axis is relatively large and generally exceeds 10 mm, and its dimensions in the other two short axes range from 2 mm to 3 mm (taking the ultrasound frequency of 1 MHz as an example), so that the focal region has a relatively large size, which affects the focusing of energy, and is unfavorable for ensuring the safety of treatment. In addition, ultrasound emitted by the existing ultrasonic transducer may be scattered or reflected by non-uniform tissues such as bones, organs containing air, and the like, making the ultrasound propagate in a seriously nonlinear manner, which in turn damages tissues in the beam path, causes an unpredictable deviation and distortion of the focal region, and influences the positioning of the focal region.

Due to the disadvantages of the existing ultrasonic transducers, their application in therapy is limited. For example, prostate hyperplasia and prostate cancer are common diseases for adult men, and the incidence of prostate hyperplasia among men aged 40 years to 79 years in China is about 50%, and the incidence of prostate hyperplasia among men aged over 80 years is 80%. However, the prostate is located in the pelvic cavity, and there are a lot of non-uniform tissues such as bones, organs containing air, and the like around the prostate, so that ultrasound emitted from the outside of a body can hardly be focused at the prostate accurately through the non-uniform tissues. Therefore, for the existing focused ultrasound treatment for prostate diseases, an ultrasonic transducer needs to be introduced into a body through the urethra or rectum, which causes discomfort to patients and easily causes damage to the urethra or rectum, and because the ultrasonic transducer has a limited size, low energy and difficulty in movement, the effect, efficiency and integrity of the treatment are poor. Meanwhile, because the existing focal region of ultrasound is cigar-shaped, it is difficult to accurately limit the focal region to a required position, and when one part of the focal region is positioned at a diseased tissue, other part of the focal region is very likely to exceed the diseased tissue and positioned at a normal tissue and may cause damage to the normal tissue, so that the treatment safety is reduced.

SUMMARY OF THE INVENTION

The present disclosure at least partially solves the problems of poor treatment effect, efficiency and safety of the existing focused ultrasound treatment device for prostate diseases, and provides an extracorporeal focused ultrasound treatment device for pelvic diseases, which has high treatment efficiency, good effect and good safety.

As a technical solution adopted to solve the technical problem of the present disclosure, there is provided an extracorporeal focused ultrasound treatment device for pelvic diseases, which includes an ultrasonic transducer and a treatment couch, wherein
the ultrasonic transducer includes a sound emitting surface and a sound generation unit that is configured to generate an ultrasonic wave; the sound emitting surface is a spherical surface having a first notch, a second notch and a third notch, a sphere corresponding to the spherical surface has a diameter in a range of 400 mm to 800 mm, one great circle of the sphere is a main great circle, the first notch and the second notch are respectively positioned at two intersections of the spherical surface and a diameter perpendicular to the main great circle, and the third notch connects the first notch with the second notch; within distances of 100 mm to 200 mm from the main great circle respectively at both sides of the main great circle, a cross-section of the sound emitting surface parallel to the main great circle is in a shape of an arc, an opening of the arc corresponds to the third notch, and a central angle corresponding to the arc is larger than 180 degrees and smaller than 300 degrees; and the sound emitting surface is capable of reflecting ultrasound, and an ultrasonic wave generated by the sound generation unit is focused at a center of the sphere corresponding to the sound emitting surface.

The treatment couch is configured for a human body to lie in a lithotomy position, and when the human body lies in the lithotomy position on the treatment couch, a pelvic cavity of the human body is positioned at the center of the sphere corresponding to the sound emitting surface with two legs of the human body respectively sticking out of the sound emitting surface through the first notch and the second notch, and an upper part of the human body sticking out of the sound emitting surface through the third notch.

Optionally, an edge of the first notch and an edge of the second notch are in a first plane and a second plane, respectively.

Optionally, the first plane and the second plane are both parallel to the main great circle.

Optionally, a distance between the first plane and the second plane is in a range of 200 mm to 400 mm.

Optionally, a distance between the first plane and the main great circle is equal to a distance between the second plane and the main great circle.

Optionally, the diameter of the sphere corresponding to the sound emitting surface is in a range of 420 mm to 600 mm; and within distances of 100 mm to 150 mm from the main great circle respectively at both sides of the main great circle, the central angle corresponding to the arc in the cross-section of the sound emitting surface parallel to the main great circle is larger than 180 degrees and smaller than 300 degrees.

Optionally, each cross-section of the sound emitting surface parallel to the main great circle is in a shape of an arc, and the central angle corresponding to the arc is larger than 200 degrees and smaller than 260 degrees.

Optionally, the opening of the arc in each cross-section of the sound emitting surface parallel to the main great circle is oriented in a same direction, and the central angle corresponding to the arc is equal.

Optionally, the sound emitting surface is symmetric with respect to the main great circle.

Optionally, when the human body lies on the treatment couch in the lithotomy position, ultrasound emitted from a first region of the sound emitting surface enters the pelvic cavity through abdomen of the human body.

When the human body lies on the treatment couch in the lithotomy position, ultrasound emitted from a second region of the sound emitting surface enters the pelvic cavity through an area between coccyx and pubic symphysis of the human body.

Optionally, the extracorporeal focused ultrasound treatment device for pelvic diseases further includes:
 a first B-mode ultrasonic probe configured to emit imaging ultrasound from the first region of the sound emitting surface to the pelvic cavity through the abdomen of the human body to form an image of the pelvic cavity; and/or
 a second B-mode ultrasonic probe configured to emit imaging ultrasound from the second region of the sound emitting surface to the pelvic cavity through perineum of the human body to form an image of the pelvic cavity.

Optionally, the treatment couch and the ultrasonic transducer are separated structures; and
 the extracorporeal focused ultrasound treatment device for pelvic diseases further includes a movement unit configured to cause the treatment couch to be close to or far away from the ultrasonic transducer.

Optionally, the extracorporeal focused ultrasound treatment device for pelvic diseases further includes:
 a medium containing unit configured to keep a sound transmission medium between a surface of the human body and the sound emitting surface.

Optionally, the extracorporeal focused ultrasound treatment device for pelvic diseases further includes:
 a driving unit configured to drive the ultrasonic transducer to move relative to the treatment couch.

Optionally, the extracorporeal focused ultrasound treatment device for pelvic diseases further includes:
 an imaging unit configured to form an image of the pelvic cavity.

Optionally, the ultrasound generated by the sound generation unit has a frequency in a range of 0.4 MHz to 1.5 MHz.

Optionally, an acoustical power of the ultrasound generated by the sound generation unit is in a range of 0 W to 1200 W.

Optionally, the acoustical power of the ultrasound generated by the sound generating unit is in a range of 0 W to 800 W.

The extracorporeal focused ultrasound treatment device for pelvic diseases adopts a specific C-shaped ultrasonic transducer, and the focal region of the ultrasonic transducer has a shape close to a sphere, a small size and high energy density, so that the device has good treatment effect, high efficiency, little influence on normal tissues and good safety; moreover, non-uniform tissues such as bones and the like have little influence on the focusing effect of the ultrasound generated by the ultrasonic transducer, and in the meanwhile, the human body lies on his/her back on the treatment couch in a specific position such that the pelvic cavity is positioned near the focal region of the ultrasonic transducer, so as to allow the ultrasound to enter the human body with maximized beam path. Therefore, the extracorporeal focused ultrasound treatment device for pelvic diseases can treat diseases of organs in the pelvic cavity by way of externally focusing ultrasonic waves, so that the size of the ultrasonic emitting surface (i.e., the sound emitting surface) of the ultrasonic transducer can be larger, and under the condition that the ultrasonic energy emitted per unit area is the same, the area of the acoustic window for ultrasound to enter the human body can be larger, and the energy density obtained at the focal region is higher. As a result, the treatment effect is improved, the treatment efficiency is improved, the treatment comfort is improved, the operation convenience is improved, the harm to the human body is reduced, and the treatment safety is improved.

The extracorporeal focused ultrasound treatment device for pelvic diseases is suitable for treating diseases of organs in a pelvic cavity, such as prostate cancer, prostate hyperplasia, hysteromyoma, adenomyosis, cervical cancer, ovarian cancer, rectal cancer, colon cancer and the like, and is particularly suitable for treating prostate diseases.

Figure 1:
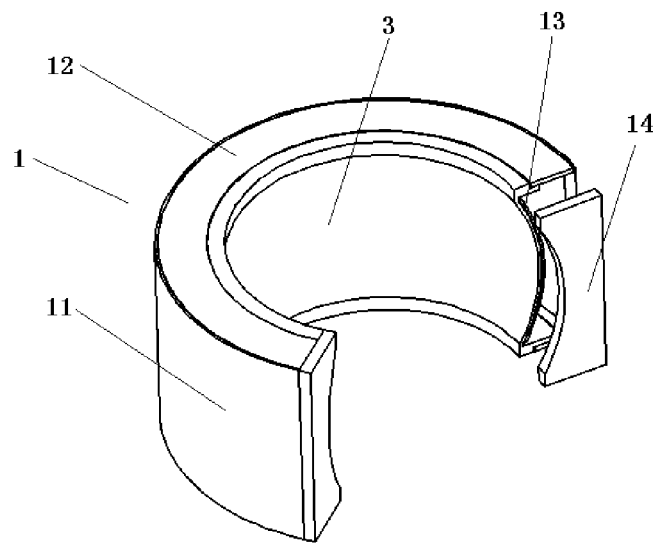
FIG. 1 is a schematic structural diagram of an ultrasonic transducer according to an embodiment of the present disclosure.

Reference numerals: 1. ultrasonic transducer; 11. housing; 12. upper cover; 13. piezoelectric array element; 14. end cover; 2. treatment couch; 3. sound emitting surface; 31. first notch; 32. second notch; 33. third notch; 35. first region; 36. second region; 41. first B-mode ultrasonic probe; 42. second B-mode ultrasonic probe; 91. first plane; 92. second plane; 99. main great circle; 01. imaging unit; 02. driving unit; 03. medium containing unit; 04. movement unit; 05. sound generation unit.

DESCRIPTION OF THE INVENTION

In order that those skilled in the art can better understand the technical solutions of the present disclosure, the present disclosure will be further described in detail below with reference to the accompanying drawings and specific implementations.

First Embodiment

As shown in FIGS. 1 to 17, the present embodiment provides an extracorporeal focused ultrasound treatment device for pelvic diseases.

The extracorporeal focused ultrasound treatment device for pelvic diseases adopts an ultrasonic transducer 1 in a specific form, and when a human body lies in a lithotomy position such that a pelvic cavity enters the ultrasonic transducer 1, ultrasound emitted by the ultrasonic transducer 1 can be focused at a specific position in the pelvic cavity of the human body to treat a disease of an organ in the pelvic cavity, such as prostate cancer, prostate hyperplasia, hysteromyoma, adenomyosis, cervical cancer, ovarian cancer, rectal cancer, colon cancer or the like, and the extracorporeal focused ultrasound treatment device for pelvic diseases is particularly suitable for treating prostate diseases.

The extracorporeal focused ultrasound treatment device for pelvic diseases of the embodiment includes an ultrasonic transducer 1 and a treatment couch 2.

The ultrasonic transducer 1 includes a sound emitting surface 3 and a sound generation unit 05 that is configured to generate an ultrasonic wave; the sound emitting surface 3 is a spherical surface having a first notch 31, a second notch 32 and a third notch 33, a sphere corresponding to the spherical surface has a diameter in a range of 400 mm to 800 mm, one great circle of the sphere is taken as a main great circle 99, the first notch 31 and the second notch 32 are respectively positioned at two intersections of the spherical surface and a diameter perpendicular to the main great circle 99, and the third notch 33 connects the first notch 31 with the second notch 32; within distances of 100 mm to 200 mm from the main great circle 99 respectively at both sides of the main great circle 99, a cross-section of the sound emitting surface 3 parallel to the main great circle 99 is in a shape of an arc, an opening of the arc corresponds to the third notch 33, and a central angle corresponding to the arc is larger than 180 degrees and smaller than 300 degrees; and the sound emitting surface 3 is capable of reflecting ultrasound, and an ultrasonic wave generated by the sound generation unit 05 is focused on a center of the sphere corresponding to the sound emitting surface 3.

The treatment couch 2 is configured for a human body to lie in a lithotomy position, and when the human body lies in the lithotomy position on the treatment couch 2, the center of the sphere corresponding to the sound emitting surface 3 is positioned in a pelvic cavity of the human body, two legs respectively stick out of the sound emitting surface 3 through the first notch 31 and the second notch 32, and an upper part of the body sticks out of the sound emitting surface 3 through the third notch 33.

The extracorporeal focused ultrasound treatment device for pelvic diseases of the embodiment has an ultrasonic transducer 1, and the ultrasonic transducer 1 has a sound generation unit 05, which is a device capable of generating ultrasound. For example, the material of the sound generation unit 05 may include piezoelectric ceramics, 1-3 type piezoelectric composite material, or the like. The shape, number, position, and other parameters of the sound generation unit 05 may be designed such that the sound generation unit 05 can emit ultrasound from all positions of the sound emitting surface 3, and the ultrasound emitted at each position propagates along the normal direction of the sound emitting surface 3 at the position, and the ultrasound can be finally focused (including directly focused or focused after being reflected) at a required position.

In an embodiment, as shown in FIG. 1, the sound emitting surface 3 may be an acoustically transparent surface with a predetermined shape, and the sound generation unit (e.g., a piezoelectric array element 13) may be disposed behind the sound emitting surface 3; alternatively, the sound emitting surface 3 may be the emitting surface of the sound generation unit itself.

Figure 17:
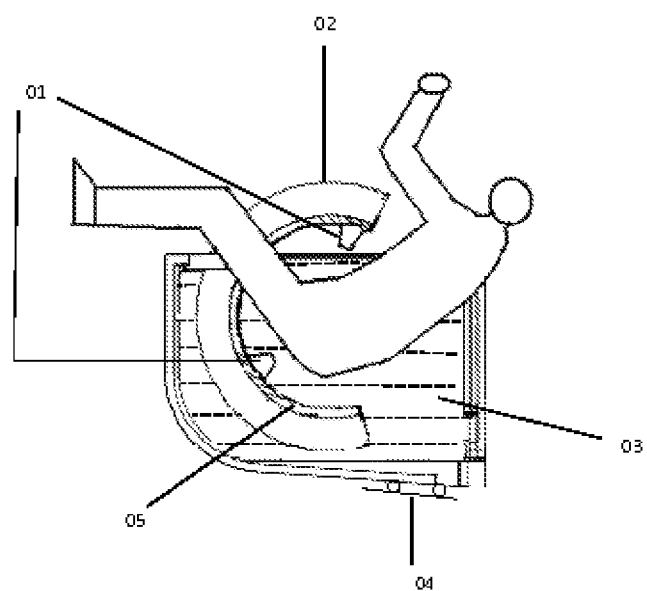
FIG. 17 is another schematic side view of a structure of an extracorporeal focused ultrasound treatment device for pelvic diseases in a combination state and with a human body according to an embodiment of the present disclosure.

In an embodiment, as shown in FIG. 17, the sound generation unit 05 may also take different forms. For example, the sound generation unit 05 may be a plurality of piezoelectric array elements 13 (e.g., rectangular piezoelectric ceramic plates) disposed at different positions of the sound emitting surface 3, that is, the plurality of piezoelectric array elements 13 are spliced together to form the sound emitting surface 3; alternatively, the sound generation unit 05 may also have the same shape as the sound emitting surface 3 (e.g., the sound generation unit 05 is a specially shaped piezoelectric ceramic plate).

Needless to say, as shown in FIG. 1, the ultrasonic transducer 1 may further include, in addition to the sound emitting surface 3 and the sound generation unit 05, a driving circuit for the sound generation unit 05, a casing (e.g., the casing of the sound generation unit 05 may include a housing 11, an upper cover 12, a lower cover, an end cover 14, etc.) for enclosing the driving circuit and the sound generation unit 05, and other components, which will not be described in detail herein.

Unlike the conventional sound emitting surface in the shape of a spherical cap, the sound emitting surface 3 of the ultrasonic transducer 1 of the present embodiment is equivalent to a spherical surface lacking three portions, and the spherical surface may have a diameter in the range of 400 mm to 800 mm, preferably in the range of 420 mm to 600 mm.

Figure 2:
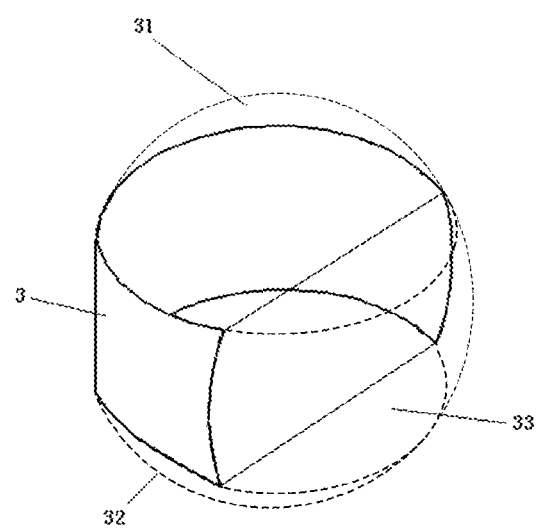
FIG. 2 is a schematic structural diagram of a sound emitting surface in an ultrasonic transducer according to an embodiment of the present disclosure.
Figure 3:
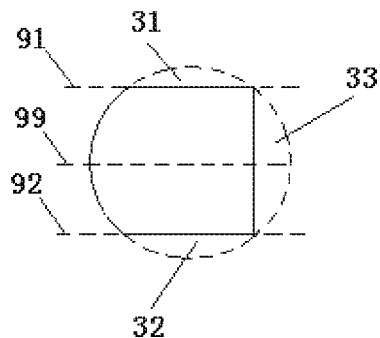
FIG. 3 is a schematic diagram of a structure, in a direction parallel to a main great circle, of a sound emitting surface of an ultrasonic transducer according to an embodiment of the present disclosure.
Figure 4:
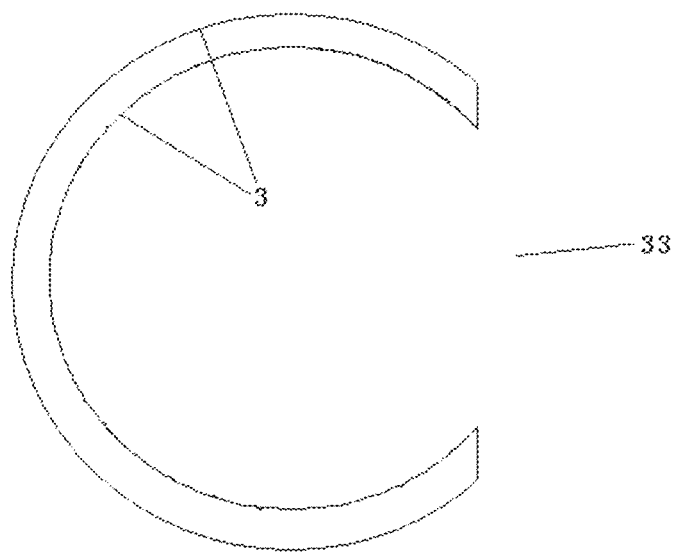
FIG. 4 is a schematic diagram of a structure, in a direction perpendicular to a main great circle, of a sound emitting surface of an ultrasonic transducer according to an embodiment of the present disclosure.

As shown in FIGS. 2 to 4, two portions (the first notch 31 and the second notch 32) missing from the sound emitting surface 3 are portions of the spherical surface at both ends of one diameter, and a great circle (i.e., a plane passing through the spherical center) perpendicular to the diameter is the main great circle 99. The third portion (third notch 33) missing from the sound emitting surface 3 is a portion laterally connecting the first notch 31 with the second notch 32.

That is, if the plane in which the main great circle 99 is located is in a horizontal direction, and the diameter perpendicular to the main great circle 99 is in a vertical direction, parts of the top end and the bottom end of a spherical surface in the vertical direction may be cut off, respectively, then a part of one side of the spherical surface may be cut off, and the cut-off part of the side should connect the cuts of the top end and the bottom end, so that the remaining spherical surface is the sound emitting surface 3.

Within the distances of 100 mm to 200 mm (preferably 100 mm to 150 mm, and the distances at two sides may be different) from the main great circle 99 respectively at the two sides of the main great circle 99, a cross-section of the sound emitting surface 3 parallel to the main great circle 99 is in the shape of an arc, the central angle corresponding to the arc is greater than 180 degrees and less than 300 degrees, and preferably, greater than 200 degrees and less than 260 degrees, and the opening of the arc corresponds to the third notch 33. That is, at least within a certain distance from the main great circle 99, the portion of the spherical surface cut off by the third notch 33 has a limited range and the central angle corresponding to the remaining portion is within the above range.

Figure 5:
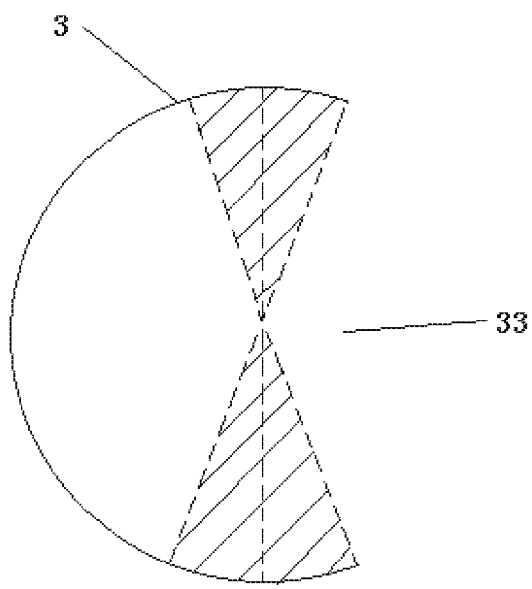
FIG. 5 is a schematic structural diagram of a cross-section of a sound emitting surface parallel to a main great circle in an ultrasonic transducer according to an embodiment of the present disclosure.

Furthermore, the sound emitting surface 3 has the capability of reflecting ultrasound, and at at least part of positions, the third notch 33 only cuts off a spherical surface smaller than half spherical surface. Therefore, as shown in FIG. 5, ultrasound emitted from a part of the arc at an angle exceeding the central angle of 180 degrees is reflected by an opposite part of the sound emitting surface 3, and the part of the arc at the angle exceeding the central angle of 180 degrees may also reflect ultrasound emitted from the opposite part of the sound emitting surface 3, so that ultrasound can return in partial region (the region filled with oblique lines in FIG. 5), so as to form a standing wave, thereby changing the focusing condition and the focal region form of ultrasound; meanwhile, the ultrasound emitted from the part of the arc corresponding to the opening is not reflected, so that ultrasound emitted from this part of the arc is still a traveling wave.

That is, the ultrasound generated by the ultrasound transducer 1 of the present embodiment is actually in the form of a combination of a traveling wave with a standing wave, and thus its propagation and focusing will change. Specifically, the ultrasonic transducer 1 can compress the major axis of the original cigar-shaped focal region, so that the focal region has a shape closer to a spherical shape and has a smaller size, the energy density is improved, the treatment effect and efficiency are improved, the damage to normal tissues is reduced, and the safety is improved. Meanwhile, the ultrasonic transducer 1 can also reduce the adverse effects of non-uniformity of tissues and bone tissues and the like on the focusing of ultrasound when the ultrasound propagates in a human body, and reduce deviation and distortion of the focal region, which facilitates accurate positioning of the focal region.

In an embodiment, edges of the first notch 31 and the second notch 32 are located in a first plane 91 and a second plane 92, respectively. In an embodiment, the first plane 91 and the second plane 92 are both parallel to the main great circle 99.

As shown in FIG. 3, in an embodiment, the first notch 31 and the second notch 32 are spherical caps cut off by planes. In an embodiment, the first notch 31 and the second notch 32 are spherical caps cut off by two parallel planes, that is, the bottom surfaces of the two cut-off spherical caps are parallel to each other. As such, the spherical surface excluding the first notch 31 and the second notch 32 is equivalent to a structure formed by butting the bottom surfaces of two spherical segments. Needless to say, the bottom surfaces of the two spherical segments are the main great circle 99, and the two spherical segments may have different heights. The sound emitting surface 3 in this form has a shape similar to a spherical segment, and is regular and simple in structure.

Needless to say, it is also feasible that the first notch 31 and second notch 32 are cut off by planes that are not parallel to each other, or by curved surfaces that are not planar.

In an embodiment, the distance between the first plane 91 and the second plane 92 ranges from 200 mm to 400 mm. In an embodiment, the distance between the first plane 91 and the second plane 92 ranges from 200 mm to 300 mm.

That is, the distance between the first notch 31 and the second notch 32 (i.e., the dimension of the sound emitting surface 3 in the vertical direction) is preferably in the above range (of course, the diameter of the sphere corresponding to the sound emitting surface 3 should be larger than the distance). Such sound emitting surface 3 has a sufficient area to generate ultrasound suitable for treatment and a size that is not too large, and can allow legs of the human body to stick out.

In an embodiment, the distance between the first plane 91 and the main great circle 99 is equal to the distance between the second plane 92 and the main great circle 99.

That is, the first notch 31 and the second notch 32 are preferably obtained by cutting with two planes that have a same distance to the center of the sphere, so that the two notches have a same size and are symmetrically distributed, which facilitates symmetry of the focal region and placement of the legs of the human body.

Needless to say, it is also possible that the first notch 31 and the second notch 32 have different distances to the center of the sphere, or have different shapes.

In an embodiment, any cross-section of the sound emitting surface 3 parallel to the main great circle 99 is in the shape of an arc, and the central angle corresponding to the arc is greater than 180 degrees and less than 300 degrees.

It is defined above that the sound emitting surface 3 is arc-shaped in a cross-section parallel to the main great circle 99 at least in the vicinity of the main great circle 99. In an embodiment, any cross-section of the sound emitting surface 3 parallel to the main great circle 99 may be in the shape of the arc, thereby ensuring that the sound emitting surface 3 can generate a standing wave at each position in the vertical direction.

Needless to say, it is also possible that the cross-section of the sound emitting surface 3 parallel to the main great circle 99 is not in the shape of an arc (e.g., is two separate arcs) at some positons.

In an embodiment, the arcs of the sound emitting surface 3 in any cross-sections thereof parallel to the main great circle 99 have openings orientated in a same direction, and correspond to central angles that are equal.

That is, at different positions in the vertical direction, the third notch 33 is orientated in the same direction, and corresponds to a same central angle. That is, the third notch 33 is preferably obtained by cutting with a plane perpendicular to the main great circle 99.

As shown in FIG. 4, the sound emitting surface 3 is shaped like the letter "C" as viewed in a direction perpendicular to the main great circle 99.

In an embodiment, the sound emitting surface 3 is symmetrical with respect to the main great circle 99.

As shown in FIG. 3, the sound emitting surface 3 is preferably symmetrical with respect to the main great circle 99, that is, parts of the sound emitting surface 3 respectively on both sides of the main great circle 99 are preferably of the same form, so that the sound field and focal region formed by the sound emitting surface are also symmetrical with respect to the main great circle 99, and are more regular and easy to control.

As shown in FIGS. 6 to 11, the treatment couch 2 is configured to support a human body during treatment. In an embodiment, a person lies on his/her back on the treatment couch 2, with the legs raised and spread to the sides, i.e., in a lithotomy position.

Figure 10:
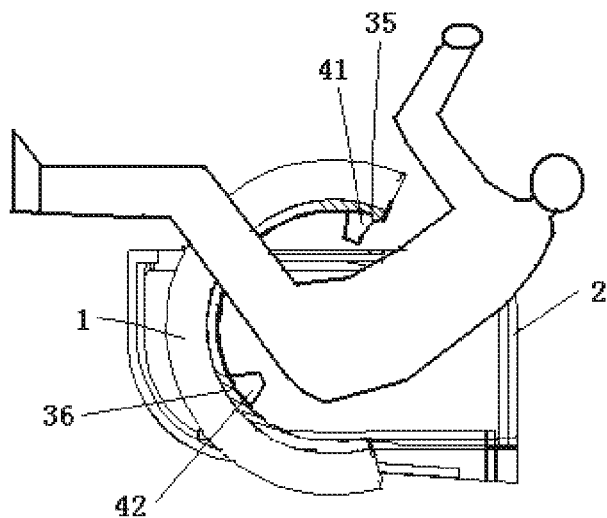
FIG. 10 is a schematic side view of a structure of an extracorporeal focused ultrasound treatment device for pelvic diseases in a combination state and with a human body according to an embodiment of the present disclosure.
Figure 11:
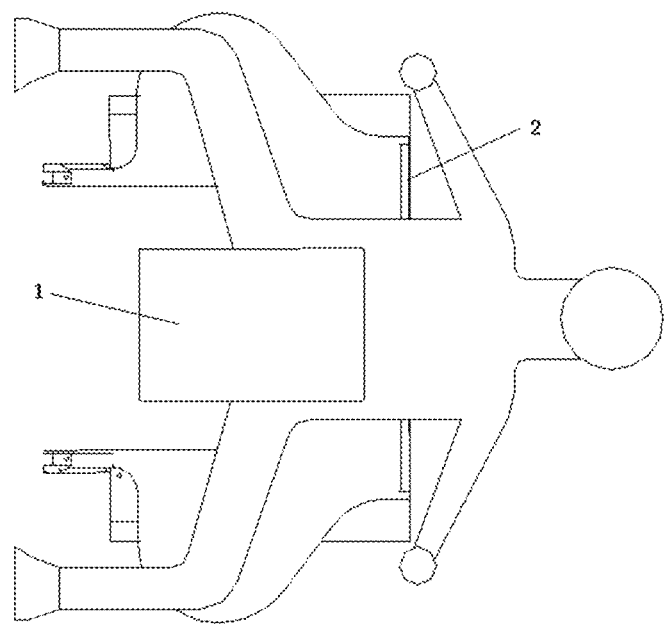
FIG. 11 is a schematic top view of a structure of an extracorporeal focused ultrasound treatment device for pelvic diseases in a combination state and with a human body according to an embodiment of the present disclosure.

Thus, as shown in FIGS. 10 and 11, in a case where the third notch 33 of the ultrasonic transducer 1 is directed toward the treatment couch 2 and the first notch 31 and the second notch 32 are respectively directed toward both sides, when the center of the sphere is located in the pelvic cavity of a human body, the upper part of the human body can stick out of the sound emitting surface 3 through the third notch 33, and at the same time, both legs of the human body can also stick out of the sound emitting surface 3 through the first notch 31 and the second notch 32, respectively.

It can be seen that if such a posture is required between the human body and the ultrasonic transducer 1, the size and the central angle of the ultrasonic transducer 1 (the sound emitting surface 3) need to meet certain requirements, and the above limitation on the parameters of the sound emitting surface 3 just enables the ultrasonic transducer 1 to be adapted to the human body.

Needless to say, in order to allow a human body to lie on the treatment couch 2 in a lithotomy position, the treatment couch 2 should have a chair, a leg support, etc., which will not be described in detail herein.

Needless to say, in an actual extracorporeal focused ultrasound treatment device for pelvic diseases, the ultrasound transducer 1 cannot be suspended, and a corresponding housing, a supporting structure, a driving circuit, etc. should be provided, but for simplicity, these structures are not shown in the drawings.

The extracorporeal focused ultrasound treatment device for pelvic diseases of the embodiment adopts a specific C-shaped ultrasonic transducer 1, and the focal region of the ultrasonic transducer 1 has a shape close to a sphere, a small size and high energy density, so that the extracorporeal focused ultrasound treatment device for pelvic diseases has good treatment effect, high efficiency, small influence on normal tissues and good safety.

Moreover, non-uniform tissues such as bones and the like have little influence on propagation of the ultrasound generated by the ultrasonic transducer 1, in the meanwhile, a human body lies on the back on the treatment couch 2 in a specific body position and a specific tissue organ in the pelvic cavity is positioned near the focal region of the ultrasonic transducer 1, so that the ultrasound is allowed to enter the pelvic cavity of the human body with maximized beam path, and the treatment of a specific lesion on a specific tissue organ in the pelvic cavity is facilitated.

Thus, the extracorporeal focused ultrasound treatment device for pelvic diseases can treat diseases of organs in the pelvic cavity by way of externally focusing ultrasonic waves, so that the size of the ultrasonic emitting surface (i.e., the sound emitting surface 3) of the ultrasonic transducer can be larger, and under the condition that the ultrasonic energy emitted per unit area is the same, the area of the acoustic window for ultrasound to enter the human body can be larger, and the energy density obtained at the focal region is higher. As a result, the treatment effect is improved, the treatment efficiency is improved, the treatment comfort is improved, the operation convenience is improved, the harm to the human body is reduced, and the treatment safety is improved.

In an embodiment, as shown in FIGS. 17, the treatment couch 2 and the ultrasonic transducer 1 may be separated structures; the extracorporeal focused ultrasound treatment device for pelvic diseases also includes a movement unit 04 configured to make the treatment couch 2 and the ultrasonic transducer 1 closer to or farther away from each other.

Figure 6:
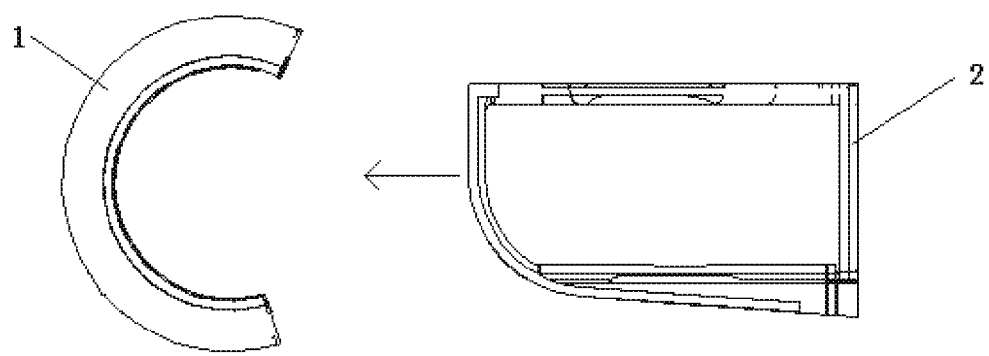
FIG. 6 is a schematic side view of a structure of an extracorporeal focused ultrasound treatment device for pelvic diseases in a split state according to an embodiment of the present disclosure.
Figure 7:
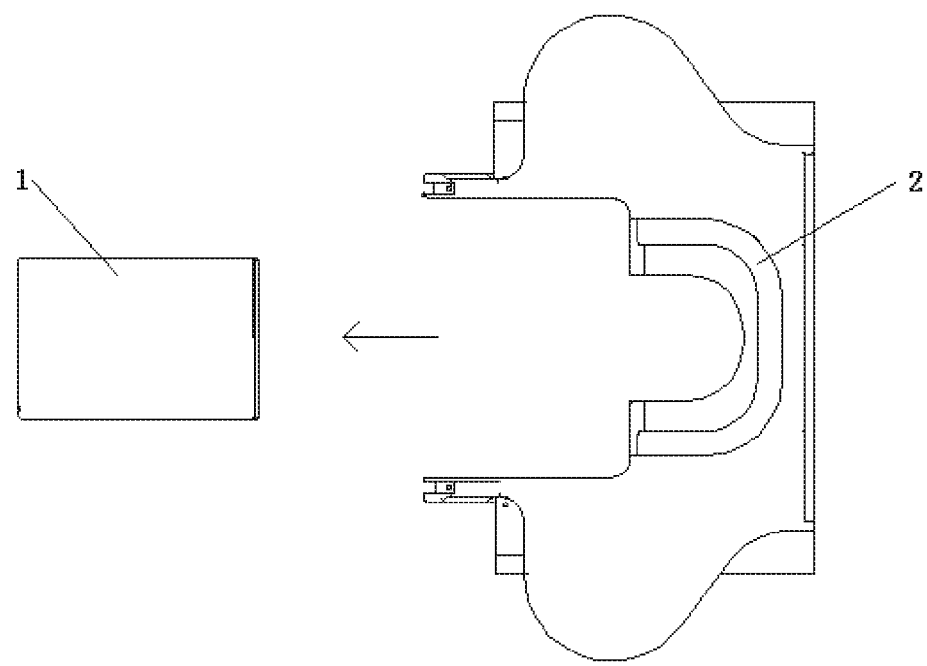
FIG. 7 is a schematic top view of a structure of an extracorporeal focused ultrasound treatment device for pelvic diseases in a split state according to an embodiment of the present disclosure.
Figure 8:
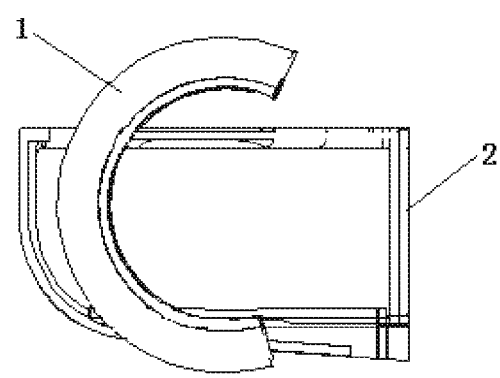
FIG. 8 is a schematic side view of a structure of an extracorporeal focused ultrasound treatment device for pelvic diseases in a combination state according to an embodiment of the present disclosure.
Figure 9:
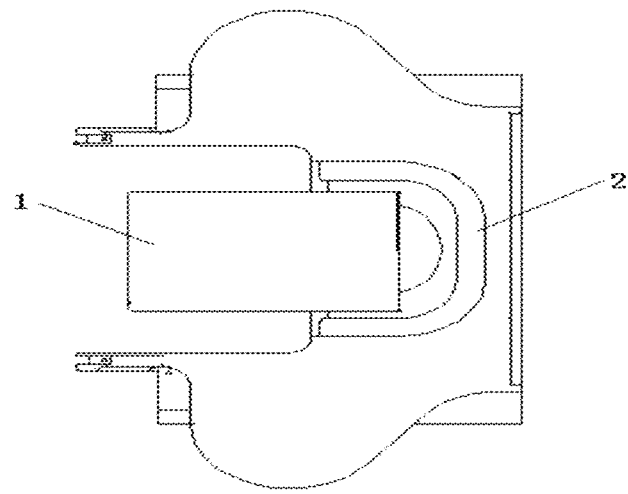
FIG. 9 is a schematic top view of a structure of an extracorporeal focused ultrasound treatment device for pelvic diseases in a combination state according to an embodiment of the present disclosure.

As shown in FIGS. 10 and 11, according to the above parameters of the sound emitting surface 3, when the center of the sphere corresponding to the sound emitting surface 3 of the transducer is in the pelvic cavity of a human body, the distances from the abdomen and the back of the human body to the ends of the sound emitting surface 3 are small, and therefore, if the treatment couch 2 is positioned near the ultrasonic transducer 1, it is difficult for the perineum to enter through the gap between the treatment couch 2 and the ultrasonic transducer 1. Therefore, as shown in FIGS. 6 and 7, the treatment couch 2 and the ultrasonic transducer 1 are preferably separated, and the treatment couch 2 may come closer to or farther away from the ultrasonic transducer 1 through the movement unit 04 (e.g., a wheel, a rail, etc.). In this way, the human body can lie on the treatment couch 2 in a lithotomy position when the treatment couch 2 is away from the ultrasonic transducer 1, and then the treatment couch 2 is caused to come close to the ultrasonic transducer 1 to make the perineum enter the sound emitting surface 3 through the third notch 33, thereby obtaining the structure shown in FIGS. 10 and 11.

In an embodiment, when the human body lies on the treatment couch 2 in a lithotomy position, ultrasound emitted from a first region 35 of the sound emitting surface 3 enters the pelvic cavity through the abdomen of the human body; when the human body lies on the treatment couch 2 in the lithotomy position, ultrasound emitted from a second region 36 of the sound emitting surface 3 enters the pelvic cavity through area between the coccyx and pubic symphysis of the human body.

Most part of the pelvic cavity of a human body is surrounded by pelvic bones, and the bones have a strong blocking effect on the ultrasound; in contrast, there is no bone in the abdomen, and less bones in the area (including the perineum, anus, etc.) between the coccyx and pubic symphysis, so ultrasound is less blocked when entering into the pelvic cavity through these two portions. Therefore, as shown in FIG. 10, the sound emitting surface 3 of the ultrasonic transducer 1 preferably has at least a first region 35 and a second region 36, and ultrasonic waves emitted from the two regions may respectively pass through the abdomen and the area between the coccyx and pubic symphysis to enter the pelvic cavity, so as to maximize the beam path.

Needless to say, the sound emitting surface 3 should also have a region between the first region 35 and the second region 36, and since the central angle between the first region 35 and the second region 36 is usually less than 150 degrees, as shown in FIG. 10, the sound emitting surface 3 actually should have a portion exceeding the first region 35 and the second region 36, such as a portion corresponding to the sacrum. Thus, ultrasonic waves emitted from all positions of the sound emitting surface 3 can form a better sound field together.

In an embodiment, as shown in FIG. 17, the extracorporeal focused ultrasound treatment device for pelvic diseases further includes an imaging unit 01 configured to form an image of the pelvic cavity.

That is, the extracorporeal focused ultrasound treatment device for pelvic diseases may also include an imaging unit 01 (e.g., B-mode ultrasound, CT, MRI or the combination thereof) for forming an image of the pelvic cavity, so that a lesion is positioned before treatment and an image of an area around the treated part is formed in real time during treatment, so as to evaluate the treatment effect at any time and adjust the treatment plan.

In an embodiment, the extracorporeal focused ultrasound treatment device for pelvic diseases may include:
- a first B-mode ultrasonic probe 41 configured to emit an imaging ultrasonic wave from the first region 35 of the sound emitting surface 3 to the pelvic cavity through the abdomen of the human body to form an image of the pelvic cavity;

and/or
- a second B-mode ultrasonic probe 42 configured to emit an imaging ultrasonic wave from the second region 36 of the sound emitting surface 3 to the pelvic cavity through the perineum of the human body to form an image of the pelvic cavity.

That is, B-mode ultrasound can be used to form an image of the pelvic cavity for monitoring, and since the B-mode ultrasound also achieves imaging by using ultrasound, it is also blocked by bones, so that the B-mode ultrasonic probes should also be disposed in the first region 35 and the second region 36 as shown in FIG. 10, so as to avoid bones to obtain images at these positions, to ensure clarity of the images, and to minimize the influence of the B-mode ultrasonic probe on the therapeutic ultrasound. In an embodiment, a first B-mode ultrasonic probe 41 is disposed in the first region 35 and emits, through the abdomen, ultrasound for imaging, while a second B-mode ultrasonic probe 42 is disposed at a specific position in the second region 36, i.e., emits, through the perineum (rather than the anus, etc.,) ultrasound for imaging.

Since the human body lies on his/her back in a lithotomy position, the angle between the first B-mode ultrasonic probe 41 and the vertical direction is usually about 30 degrees, and the angle between the second B-mode ultrasonic probe 42 and the vertical direction is about 80 degrees.

In an embodiment, the B-mode ultrasonic probes may be arranged at corresponding positions of the sound emitting surface 3 and perform imaging in a non-contact manner; alternatively, as shown in FIG. 10, the B-mode ultrasonic probes may protrude from the sound emitting surface 3 and may be retractable, so that one or two of the B-mode ultrasonic probes may be selected to extend out and contact with the human body as required for imaging.

It can be seen that, for the extracorporeal focused ultrasound treatment device for pelvic diseases of the embodiments, by providing the B-mode ultrasonic probes at specific positions, an ultrasonic image with the best quality can be obtained from the optimal position under the condition of reducing influence on the therapeutic ultrasound as much as possible; moreover, the B-mode ultrasonic probes are disposed on the sound emitting surface 3 (i.e., on the ultrasonic transducer 1), so that when the ultrasonic transducer 1 moves, the B-mode ultrasonic probes will move together with the ultrasonic transducer 1, and thus the B-mode ultrasonic probes aim at the optimal imaging positions at any time.

In an embodiment, as shown in FIG. 17, the extracorporeal focused ultrasound treatment device for pelvic diseases further includes a driving unit 02 for driving the ultrasonic transducer 1 to move relative to the treatment couch 2.

It is clear that the focal region of ultrasound needs to be located at the lesion position during treatment, and the accurate lesion positions are different according to the differences in body type, disease type, treatment condition and the like, and therefore, the position of the focal region needs to be adjusted in real time during the treatment. Therefore, a driving unit may be provided to drive the ultrasonic transducer 1 to move, and then to drive the focal region to move.

The movement driven by the driving unit 02 may include translations in three axial directions perpendicular to one another, and such movement may also cause the focal region to translate; alternatively, the movement may include rotating the ultrasound transducer 1 around different axial directions, so as to cause the ultrasound to enter the human body from different directions.

In an embodiment, as shown in FIG. 17, the extracorporeal focused ultrasound treatment device for pelvic diseases further includes a medium containing unit 03 for keeping a sound transmission medium between a surface of the human body and the sound emitting surface 3.

In order to reduce attenuation of ultrasound during its propagation in air, a sound transmission medium such as deaerated water may be provided between the sound emitting surface 3 of the ultrasound transducer 1 and the human body, and for this reason, a medium containing unit 03 capable of holding a sound transmission medium (e.g., deaerated water) is preferably provided to cause the space between the sound emitting surface 3 of the ultrasound transducer 1 of the present embodiments and the surface of the human body through which ultrasound is to pass to be filled with the sound transmission medium, and the medium containing unit 03 may be in the form of a water basin or the like, and will not be described in detail herein.

In an embodiment, the ultrasound generated by the sound generation unit has a frequency in the range of 0.4 MHz to 1.5 MHz.

In the embodiment, the ultrasound generated by the sound generation unit has an acoustical power in the range of 0 W to 1200 W. In an embodiment, the acoustical power of the ultrasound generated by the sound generation unit ranges from 0 W to 800 W.

For the ultrasonic transducer 1 in any one of the above forms, when it is used for treating a disease of an organ in the pelvic cavity, the parameters of the ultrasound emitted by the ultrasonic transducer 1 are preferably in the above ranges to achieve good treatment effect.

Figure 12:
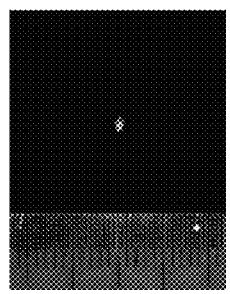
FIG. 12 is a photograph of a cavitated region formed at a focal point in a free field by an extracorporeal focused ultrasound treatment device for pelvic diseases according to an embodiment of the present disclosure.

The extracorporeal focused ultrasound treatment device for pelvic diseases of the embodiments emits ultrasonic waves at an acoustical power of 200 W toward deaerated water, so as to cavitate water in the focal region, and a photograph of the cavitated region taken from the first notch 31 is shown in FIG. 12. It can be seen that the cavitated region (i.e., the focal region) in the photograph has a shape close to a circle, a size of 1.8 mm*1.2 mm, and a length-width ratio of 3:2, which indicates that, compared with the conventional focused ultrasound transducer with only traveling waves, the extracorporeal focused ultrasound treatment device for pelvic diseases of the embodiments has a focused ultrasound transducer having a focal region whose major axis is significantly compressed, whose shape changes from a cigar shape to an approximately spherical shape, and which has a reduced size, an increased energy density, and a more regular shape.

Figure 13:
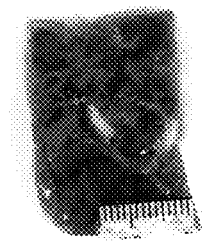
FIG. 13 is a photograph of a necrotic area of biological tissues formed after an extracorporeal focused ultrasound treatment device for pelvic diseases according to an embodiment of the present disclosure performs ultrasound irradiation on an exvivo bovine liver.

When the extracorporeal focused ultrasound treatment device for pelvic diseases of the embodiments is used to treat an exvivo bovine liver with ultrasound irradiation at an acoustical power of 400 W for 2 seconds, as shown in FIG. 13, a target area with a depth of 80 mm is obviously damaged in a short time, and the damaged part is in a fusiform shape, and has a clear boundary, a size of 4.4 mm*1.5 mm, and a length-width ratio of less than 3:1, which is lower than the length-width ratio (generally greater than 5:1) of the damaged part caused by a conventional focused ultrasound transducer. This also indicates that the focal region of the extracorporeal focused ultrasound treatment device for pelvic diseases of the present embodiments has a more regular shape.

Figure 14:
FIG. 14 is a diagram of a test device for performing ultrasonic irradiation on an exvivo bovine muscle in a pelvic bone with an extracorporeal focused ultrasound treatment device for pelvic diseases according to an embodiment of the present disclosure.
Figure 15:
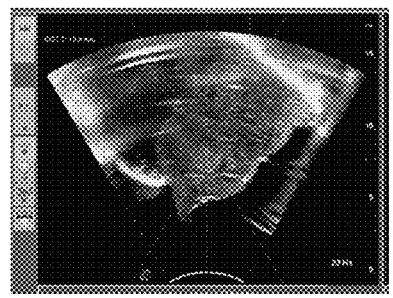
FIG. 15 is a B-mode ultrasonic image of an exvivo bovine muscle in a pelvic bone on which an extracorporeal focused ultrasound treatment device for pelvic diseases according to an embodiment of the present disclosure is performing ultrasonic irradiation.
Figure 16:
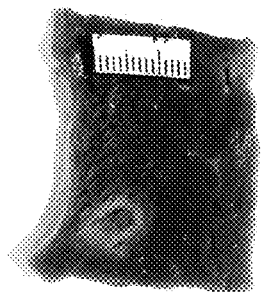
FIG. 16 is a photograph of a necrotic area of biological tissues formed after an extracorporeal focused ultrasound treatment device for pelvic diseases according to an embodiment of the present disclosure performs ultrasound irradiation on an exvivo bovine muscle tissues in a pelvic bone.

As shown in FIG. 14, a pelvic bone is placed at a preset position at an inner side of the ultrasonic transducer 1 of the extracorporeal focused ultrasound treatment device for pelvic diseases so as to simulate the position of the pelvic bone of a human body, and then an exvivo bovine muscle tissue is placed in the pelvic bone, as shown in FIG. 15. The focal region is positioned at a position equivalent to the position having a distance of 10 mm from the rectum of the human body, and a treatment process for the prostate is simulated, the ultrasonic power is 400 W, the target area has a depth of 55 mm, and the ultrasonic irradiation time is 2 seconds*5 times. As shown in FIG. 16, the bovine muscle tissue subjected to ultrasonic irradiation has an obviously damaged target area with a clear boundary, no damage is caused to the envelope, and no damage is caused to the interface between the simulated rectum and prostate. This shows that the ultrasound emitted by extracorporeal focused ultrasound treatment device for pelvic diseases of the embodiments is less affected by non-uniform tissues such as bones in a human body, can still maximize an beam path when being applied in an actual human body environment, forms a focal region with small size, excellent shape and accurate position, achieves good treatment effect and efficiency, and avoids damage to normal tissues.

It could be understood that the above implementations are merely exemplary implementations for illustrating the principle of the present disclosure, but the present disclosure is not limited thereto. Various modifications and improvements can be made by those skilled in the art without departing from the spirit and essence of the present disclosure, and these modifications and improvements are also considered to be within the protection scope of the present disclosure.

The invention claimed is:
1. An extracorporeal focused ultrasound treatment system at least capable of treating a pelvic disease, comprising an ultrasonic transducer and a treatment couch, wherein
    the treatment couch is configured for a human body to lie in a lithotomy position;
    the ultrasonic transducer comprises a sound emitting surface and a sound generation unit, wherein the sound generation unit is configured to generate an ultrasonic wave; the sound emitting surface is a concave spherical surface having a first notch, a second notch and a third notch, and the first notch and the second notch are respectively configured for two legs of the human body to stick out of the sound emitting surface; and the third notch is configured for an upper part of the human body to stick out of the sound emitting surface;
    the concave spherical surface has one main great circle, and a plane in which the main great circle is located perpendicular to a surface of the treatment couch for the human body to lie thereon; and the first notch and the second notch are respectively positioned on two sides of the plane in which the main great circle is located, and the third notch connects the first notch with the second notch;
    the concave spherical surface has a diameter in a range of 400 mm to 800 mm; cross sections of the concave spherical surface parallel to the main great circle are all in a shape of an arc; a distance from each of a plane in which the first notch is located and a plane in which the second notch is located to the plane in which the main great circle is located is in a range of 100 mm to 200 mm, and two end points of all the arcs form an edge of the third notch, and central angles corresponding to all the arcs are larger than 180 degrees and smaller than 300 degrees; and
    the sound emitting surface is capable of reflecting ultrasound, an ultrasonic wave generated by the sound generation unit is focused at a center of the sound emitting surface, and the center is configured to be corresponding to a position of a pelvic cavity of the human body.
2. The extracorporeal focused ultrasound treatment system of claim 1, wherein the first notch and the second notch are formed by cutting off cap-like portions from the concave spherical surface by a first plane and a second plane, respectively.

3. The extracorporeal focused ultrasound treatment system of claim 2, wherein the first plane and the second plane are both parallel to the plane where the main great circle is located.

4. The extracorporeal focused ultrasound treatment system of claim 3, wherein a distance between the first plane and the second plane is in a range of 200 mm to 400 mm, so as to enable the sound emitting surface to have an area sufficient to generate ultrasound suitable for treatment, and enable the first notch and the second notch to allow the two legs of the human body to stick out.

5. The extracorporeal focused ultrasound treatment system of claim 3, wherein a distance between the first plane and the plane in which the main great circle is located is equal to a distance between the second plane and the plane in which the main great circle is located.

6. The extracorporeal focused ultrasound treatment system of claim 1, wherein
the diameter of the concave spherical surface is in a range of 420 mm to 600 mm; and
within distances of 100 mm to 150 mm from the plane where the main great circle is located respectively at both sides of the main great circle, the central angle corresponding to the arc in the cross-section of the sound emitting surface parallel to the plane where the main great circle is located is larger than 180 degrees and smaller than 300 degrees, so as to enable a part of the sound emitting surface at the central angle exceeding 180 degrees to reflect ultrasound emitted by an opposite part of the sound emitting surface to form a standing wave inside a space enclosed by the sound emitting surface, thereby changing a focal region form of the ultrasound.

7. The extracorporeal focused ultrasound treatment system of claim 1, wherein each cross-section of the sound emitting surface parallel to the plane where the main great circle is located is in a shape of an arc, and the central angle corresponding to the arc is larger than 200 degrees and smaller than 260 degrees, so as to enable a part of the sound emitting surface at the central angle exceeding 180 degrees to reflect ultrasound emitted by an opposite part of the sound emitting surface to form a standing wave inside a space enclosed by the sound emitting surface, thereby changing a focal region form of the ultrasound.

8. The extracorporeal focused ultrasound treatment system of claim 7, wherein the opening of the arc in each cross-section of the sound emitting surface parallel to the plane where the main great circle is located is oriented in a same direction, and the central angle corresponding to the arc is equal.

9. The extracorporeal focused ultrasound treatment system of claim 1, wherein the sound emitting surface is symmetric with respect to the plane in which the main great circle is located.

10. The extracorporeal focused ultrasound treatment system of claim 1, wherein when the human body lies on the treatment couch in the lithotomy position, ultrasound emitted from a first region of the sound emitting surface enters the pelvic cavity through abdomen of the human body; and
when the human body lies on the treatment couch in the lithotomy position, ultrasound emitted from a second region of the sound emitting surface enters the pelvic cavity through an area between coccyx and pubic symphysis of the human body.

11. The extracorporeal focused ultrasound treatment system of claim 10, further comprising:
at least one of a first B-mode ultrasonic probe configured to emit imaging ultrasound from the first region of the sound emitting surface to the pelvic cavity through the abdomen of the human body to form an image of the pelvic cavity and a second B-mode ultrasonic probe configured to emit imaging ultrasound from the second region of the sound emitting surface to the pelvic cavity through perineum of the human body to form an image of the pelvic cavity.

12. The extracorporeal focused ultrasound treatment system of claim 1, wherein
the treatment couch and the ultrasonic transducer are separated structures; and
the extracorporeal focused ultrasound treatment system further comprises a movement unit configured to cause the treatment couch to come closer to or farther away from the ultrasonic transducer.

13. The extracorporeal focused ultrasound treatment system of claim 1, further comprising:
a medium containing unit configured to keep a sound transmission medium between a surface of the human body and the sound emitting surface.

14. The extracorporeal focused ultrasound treatment system of claim 1, further comprising:
a driving unit configured to drive the ultrasonic transducer to move relative to the treatment couch.

15. The extracorporeal focused ultrasound treatment system of claim 1, further comprising:
an imaging unit configured to form an image of the pelvic cavity.

16. The extracorporeal focused ultrasound treatment system of claim 1, wherein
the ultrasound generated by the sound generation unit has a frequency in a range of 0.4 MHz to 1.5 MHz, so as to achieve a good treatment effect on a disease of an organ in the pelvic cavity.

17. The extracorporeal focused ultrasound treatment system of claim 1, wherein
the ultrasound generated by the sound generation unit has an acoustical power larger than 0 W and less than or equal to 1200 W, so as to achieve a good treatment effect on a disease of an organ in the pelvic cavity.

18. The extracorporeal focused ultrasound treatment system of claim 17, wherein
the acoustical power of the ultrasound generated by the sound generating unit is larger than 0 W and less than or equal to 800 W, so as to achieve the good treatment effect on the disease of the organ in the pelvic cavity.

* * * * *